United States Patent [19]

Arganbright et al.

[11] Patent Number: 4,950,834

[45] Date of Patent: Aug. 21, 1990

[54] ALKYLATION OF ORGANIC AROMATIC COMPOUNDS IN A DUAL BED SYSTEM

[76] Inventors: Robert P. Arganbright; Dennis Hearn, both of P.O. Box 34687, Houston, Tex. 77034

[21] Appl. No.: 385,443

[22] Filed: Jul. 26, 1989

[51] Int. Cl.$^5$ .............................................. C07C 2/66
[52] U.S. Cl. ..................... 585/446; 585/449; 585/450; 585/467
[58] Field of Search .............. 585/449, 450, 467, 446

[56] References Cited

U.S. PATENT DOCUMENTS

| | | | |
|---|---|---|---|
| 3,851,004 | 11/1974 | Yang | 585/467 |
| 4,049,739 | 9/1977 | Zabransky et al. | 585/467 |
| 4,215,011 | 7/1980 | Smith, Jr. | 252/426 |
| 4,232,177 | 11/1980 | Smith, Jr. | 585/324 |
| 4,242,530 | 12/1980 | Smith, Jr. | 585/510 |
| 4,302,356 | 2/1981 | Smith, Jr. | 252/426 |
| 4,307,254 | 12/1981 | Smith, Jr. | 568/647 |
| 4,336,407 | 6/1982 | Smith, Jr. | 568/697 |
| 4,439,350 | 3/1984 | Jones, Jr. | 502/527 |
| 4,443,559 | 4/1984 | Smith, Jr. | 502/527 |
| 4,482,775 | 11/1984 | Smith, Jr. | 585/671 |
| 4,849,569 | 7/1989 | Smith, Jr. | 584/446 |
| 4,876,408 | 10/1989 | Ratcliffe et al. | 585/467 |

*Primary Examiner*—Glenn Caldarola
*Assistant Examiner*—William C. Diemler
*Attorney, Agent, or Firm*—Kenneth H. Johnson

[57] ABSTRACT

Cumene is produced in a catalytic distillation column reactor having an upper bed of Omega type molecular sieve catalyst and a lower bed of Y type molecular sieve catalyst. Benzene and propylene are reacted in the upper bed where the Omega type sieve is more selective to cumene that the Y type sieve. Part of the reaction mixture flows down the column to the Y bed where benzene reacts with any unreacted propylene to produce cumene. Additionally, benzene reacts with dipropylbenzene in the Y bed to produce more cumene. Cumene is recovered as bottoms product and unreacted benzene recovered as overheads where it may be returned as reflux to the column to control the mole ratio of benzene to propylene.

22 Claims, 2 Drawing Sheets

ALKYLATION OF ORGANIC AROMATIC COMPOUNDS IN A DUAL BED SYSTEM

BACKGROUND OF THE INVENTION

1. Field of The Invention

The present invention relates to a process for the alkylation of organic aromatic compounds. In particular the invention relates to the alkylation of benzene with propylene to produce cumene. More particularly the invention relates to a process for the concurrent alkylation and distillation of reaction components (reactants and products) in a catalyst bed wherein the catalyst also serves as the distillation structure. Most particularly, the catalyst utilized is a dual bed of Omega and Y type molecular sieves.

2. Related Art

Recently a new method of carrying out catalytic reactions has been developed, wherein the components of the reaction system are concurrently separable by distillation, using the catalyst structures as the distillation structures. Such systems are described variously in U.S. Pat. Nos. 4,215,011; 4,232,177; 4,242,530; 4,302,356; 4,307,254; 4,336,407; 4,439,350; 4,443,559; and 4,482,775 commonly assigned herewith.

Briefly, a structure described there is a cloth belt with a plurality of pockets spaced along the belt, which is then wound in a helix about a spacing material such as stainless steel knitted mesh. These units are then disposed in the distillation column reactor. In addition, commonly assigned U.S. Pat. Nos. 4,443,559 and 4,250,052 disclose a variety of catalyst structures for this use and are incorporated herein.

Ethylbenzene and cumene are currently produced by the reaction of benzene and the respective olefin, i.e., ethylene and propylene by acid catalysis. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large volume recycle in conventional processes. Advantages of the present invention are that the catalysts are not highly corrosive and may not require periodic regeneration, the heat of reaction is used efficiently, only low volume is required and the feed ratios can approach unity.

A catalytic distillation process for the production of cumene is disclosed in co-pending U.S. patent application Ser. No. 07/122,485, where a single bed of either acid cation exchange resin or a type Y molecular sieve catalyst was used.

The inventors herein have discovered a process for the alkylation of benzene with propylene that takes advantage of the higher selectivity of the Omega type sieves while reducing the amount of undesirable olefins in the cumene product.

SUMMARY OF THE INVENTION

Briefly, the present invention is a process for the alkylation of benzene by contacting the benzene and propylene in a distillation column reactor containing a dual bed of molecular sieve catalyst in a reaction distillation zone thereby catalytically reacting the benzene and propylene to produce an cumene product and concurrently in said fixed bed fractionating the resultant cumene product from the unreacted materials. The molecular sieve catalyst in each bed provides both the catalytic sites and the distillation sites. The cumene, having a higher boiling point, is withdrawn (rom the distillation column reactor at a point below the fixed bed and unreacted benzene and propylene (if any) may be taken off as an overhead.

Specifically the two catalyst are arranged so that the initial reaction of propylene and benzene occurs in the Omega molecular sieve bed and a reaction mixture, corresponding to the mid reflux in a single bed catalytic reaction distillation system for the reaction, is directed to a type Y molecular sieve where the reaction is completed. In other words reflux that would normally go back to the Omega bed instead goes to the type Y bed.

The feed to the type Y bed may be characterized as containing benzene, cumene, isopropylene, dipropylbenzene, tripropylbenzene, propylene dimers and other oligomers. Depending on the nature of the feed, there may be other materials present which may have some bearing on the long term or overall operation of the process, but are not of direct concern to the present invention. In addition to the apparent reaction of the dimers and/or other oligomers there is a degree of transalkylation occurring that favors the cumene production.

DETAILED DESCRIPTION OF THE INVENTION

Figure 1:
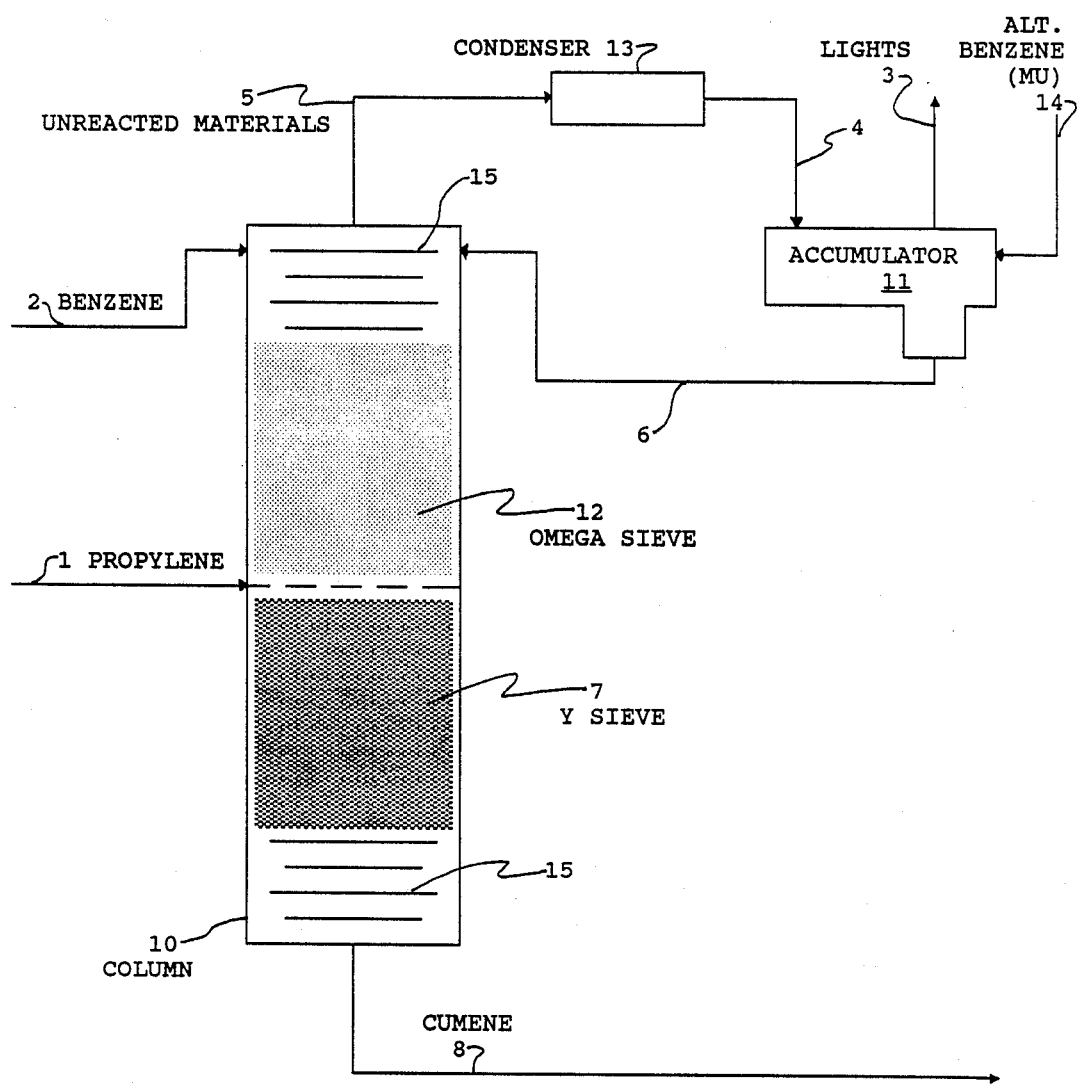
FIG. 1 is a schematic representation of a preferred embodiment of one species of the present invention for producing cumene with the catalysts in the reactor distillation column.

The Omega type molecular sieve catalyst has been found to be more selective for the production of cumene than the type Y. However, the bottoms cumene product contains an unsatisfactory amount of heavier boiling olefins. This is believed to be due to the small pore size of the Omega catalyst as compared to the type Y sieve. The smaller pore size may not allow the dimerized propylene to react with the benzene, leaving it available to react with other propylene to produce the unwanted higher boiling olefins found in the cumene product.

The dual bed system provides the additional advantage of carry over of benzene into the lower bed of Y sieve along with cumene and dimerized propylene. In that portion of the reactor the dimerized propylene can react with the benzene present and reduces the amount of unwanted heavier boiling olefins in the cumene product. Thus the higher yield of the Omega catalyst is obtained with reduced oligomerization.

The molecular sieve catalyst packing is of such a nature as to allow vapor flow through the bed, yet provide a sufficient surface area for catalytic contact as described in the previously noted U.S. Pat. Nos. 4,215,011 and 4,302,356 which are incorporated herein in their entirety. The two distinct beds are comprised of an Omega type molecular sieve and a Y type molecular sieve. The Omega sieve is disposed in the upper one-third to one-half of the distillation column reactor with the Y sieve occupying the lower portion of the reactor.

The propylene feed is added either below the lower bed of catalyst or between the two beds, but preferably between the two beds. The benzene is preferably added above the Omega sieve and may be conveniently added to the reflux as make-up or fed separately. In order to achieve high selectivity toward monosubstitution (which is a preferred aspect of the present invention), there is a large excess of benzene to propylene in the reactor in the range of 2 to 100 moles of benzene per mole of propylene. The net molar feed ratio of benzene to propylene may be close to 1:1, but the system is operated so as to maintain a substantial molar excess of benzene to propylene in the reaction zone. The cumene product is the highest boiling material and is separated in the lower portion of the column usually as bottoms. The benzene is the second highest boiling component (excluding inerts) as noted above, however, by operating with a large excess of benzene, the major portion of the propylene is reacted, thereby reducing the separation and recovery problems.

The success of catalytic distillation lies in an understanding of the principles associated with distillation. First, because the reaction is occurring concurrently with distillation, the initial reaction product is removed from the reaction zone as quickly as it is formed. The removal of the alkylation product minimizes polysubstitution and decomposition of the alkylation product. Second, because the benzene is boiling, the temperature of the reaction is controlled by the boiling point of that component at the system pressure. The heat of the reaction simply creates more boil up, but no increase in temperature. Third, the reaction has an increased driving force because the reaction products have been removed and cannot contribute to a reverse reaction (Le Chatelier's Principle).

As a result, a great deal of control over the rate of reaction and distribution of products can be achieved by regulating the system pressure. Also, adjusting the through-put (residence time a liquid hourly space velocity) gives further control of product distribution and degree of olefin conversion.

The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa. It can also be appreciated that in catalytic distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

Molecular sieves are porous crystalline, three-dimensional alumina-silicates of the zeolite mineral group. The crystal skeleton is composed of silicon and aluminum atoms each surrounded by four oxygen atoms to form the crystalline structure. The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Usually synthetic zeolites are prepared in the sodium form, that is, with a sodium cation in close proximity to each aluminum tetrahedron and balancing its charge. To date seven principal types of molecular sieves have been reported, A, X, Y, L, erionite, Omega and mordenite. The A type have relative small pore size. By the term ore size is meant the effective pore size (diameter) rather than the free pore size (diameter). Types X and Y have larger pore size (approximately 10 A.) and differ as to the range of ratio of $Al_2O_3$ to $SiO_2$ as:

Type X—$Al_2O_3$ /2.0–3.0 $SiO_2$
Type Y—$Al_2O_3$/3.0–6.0 $SiO_2$

Type L and the other types listed have still higher ratios of $SiO_2$ to $Al_2O_3$. Of particular interest is the Omega type which has an $Al_2O_3$ to $SiO_2$ ratio of 1:5 to 1:12.

The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with ammonium hydroxide to remove the Na and thereafter the mole sieve is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability. In addition to mole sieves which are acidic according to the Bronsted. Theory those mole sieves which exhibit acidic characteristics under the Lewis Theory, for example, calcium exchanged mole sieves, are suitable for the present reaction. By exchanging the univalent cations (e.g.) $Na^+$) with multivalent cations, strong ionic activity is imparted. The ratio of $SiO_2$: $Al_2O_3$ Valence and radius of the cation and the extent of exchange all affect the catalyst activity. In general activity increases with (1) increased $SiO_2$ $Al_2O_3$ ratio, (2) decreased cation radius and an increase in cation valence. The effect of replacing univalent ions (e.g. $Na^+$ with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention.

It would appear that the pore size within the crystal lattice may affect the selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal.

The acid form mole sieves are generally produced and available as particles in the range of <10 micron (powders) to 0.2 inch in diameter (beads).

In this form the mole sieves form too compact a bed and will not function adequately in a distillation, since there is a very large pressure drop through the bed and the free flow of internal reflux and rising vapor is impeded. Mole sieves in the shape of conventional distillation structures, such as rings, saddles, and the like may be used in the present invention. The particulate mole sieves may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material used to make the container is such that the catalyst is retained therein and will not pass through the openings in thermal aerial. Particles of about 0.15 mm size or powders may be used and particles up to about ¼ inch diameter may be employed in the containers.

The container employed to hold the catalyst particles may have any configuration, such as the pockets disclosed in the commonly assigned patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus desirably the spacing component or material should comprise about 30 volume % of the catalytic distillation structure, preferably about 30 volume % to 70 volume %.

Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component. In the case of larger catalyst components such as from about ¼ inch to ½ pellets, spheres, pills and the like each such larger component may be individually intimately associated with or surrounded by the spacing component as described above. It is not essential that the spacing component entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the mole sieve particles into a plurality of pockets in a cloth belt, which is supported in the distillation column reactor by open mesh knitted stainless steel wire by twisting the two together in a helical form. This allows the requisite flows and prevents loss of catalysts. The cloth may be any material which is inert in the reaction. Cotton or linen are useful, but fiber glass cloth or "Teflon" cloth are preferred.

In the following examples the catalyst packing consisted of bags in the form of a fiber glass cloth belt approximately six inches wide with narrow pockets approximately ¾ inch wide sewn across the belt. The pockets are spaced about ¼ inch apart. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the mole sieve filled cloth pockets and provide a passage for vapor flow.

The wire mesh provides the support for the catalyst (belt) and provides some degree of vapor passage through the catalyst particles which otherwise form a very compact bed which has a high pressure drop. Thus, the down flowing liquid is in intimate contact with the rising vapors in the column.

In commercial-scale operations, it is contemplated, catalyst packing would be made up of alternating layers of mole sieve filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing should be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

The preferred arrangement of the two different type mole sieve beds is to have a lower bed of type Y filling the lower one-half to two-thirds of the column with the Omega sieve filling the remainder. Although in two distinct beds, the method described above would be applied to each bed.

FIG. 1 illustrates one embodiment of the present invention. Referring to the drawing, distillation column reactor 10 is divided into two sections. In the lower section 7 the catalyst packing (catalytic distillation structures) are positioned as described. Linde molecular sieve LZ-Y82 1/16" (Union Cabide Corp.) is deposited in the pockets of fiber glass belts and formed in to a helix with stainless steel mesh as described. In the upper section 12 Union Carbide Omega type sieve is likewise loaded into the reactor 10. Conventional distillation trays or structures 15 are positioned above and below the catalyst beds.

The lower portion as well as the upper of the column may contain conventional distillation column structure (trays or inert packing) to achieve the desired final separation in the lower and upper sections of the column. In the drawing the benzene is indicated to be introduced into the column 10 via flow line 2 into the upper bed 12 it may be conveniently added as makeup into reflux accumulator 11. The propylene is fed to the column via flow line 1 at about the mid point between the two catalyst beds 7 and 12 or below the lower catalyst bed (not shown) for better mixing. The propylene may also be fed at several points to reduce the concentration at any one location in the catalyst zone, thus reducing oligomerization as a side reaction. The reaction is exothermic and initiated by contacting the two reactants in the catalyst packing. Cumene is the principal reaction product in the Omega bed 12, however dimerized propylene is also produced along with some dipropylbenzene. Since complete separation of the reaction products and benzene does not occur in the Omega bed 12, cumene, small amounts of propylene, dimerized propylene, dipropylbenzene (tripropylbenzene is also present) and benzene flow down the column into the Y bed where any propylene and the dimerized propylene may react with the benzene to produce additional cumene and prevent formation of undesired higher boiling olefins. Additionally, the dipropylbenzene is transalkylated with unreacted benzene to produce additional cumene.

The cumene product is higher boiling than benzene and propylene and is recovered via flow line 8 as a bottoms product. The feed of propylene is adjusted such that there is a molar excess of benzene in the reactor, such that the overhead 5 is primarily benzene, the propylene having been almost totally reacted. In addition to benzene and some propylene other lights go off overhead. The overhead is passed to condenser 13 which is operated to condense substantially all of the benzene which passes via flow line 4 to accumulator 11 and hence, by reflux via flow line 6 to column 10. The benzene used in the reaction and lost with the lights (which exit accumulator 11 via 3) is made up by fresh benzene feed through flow line 2 or alternatively to accumulator 4 through flow line 14.

Figure 2:
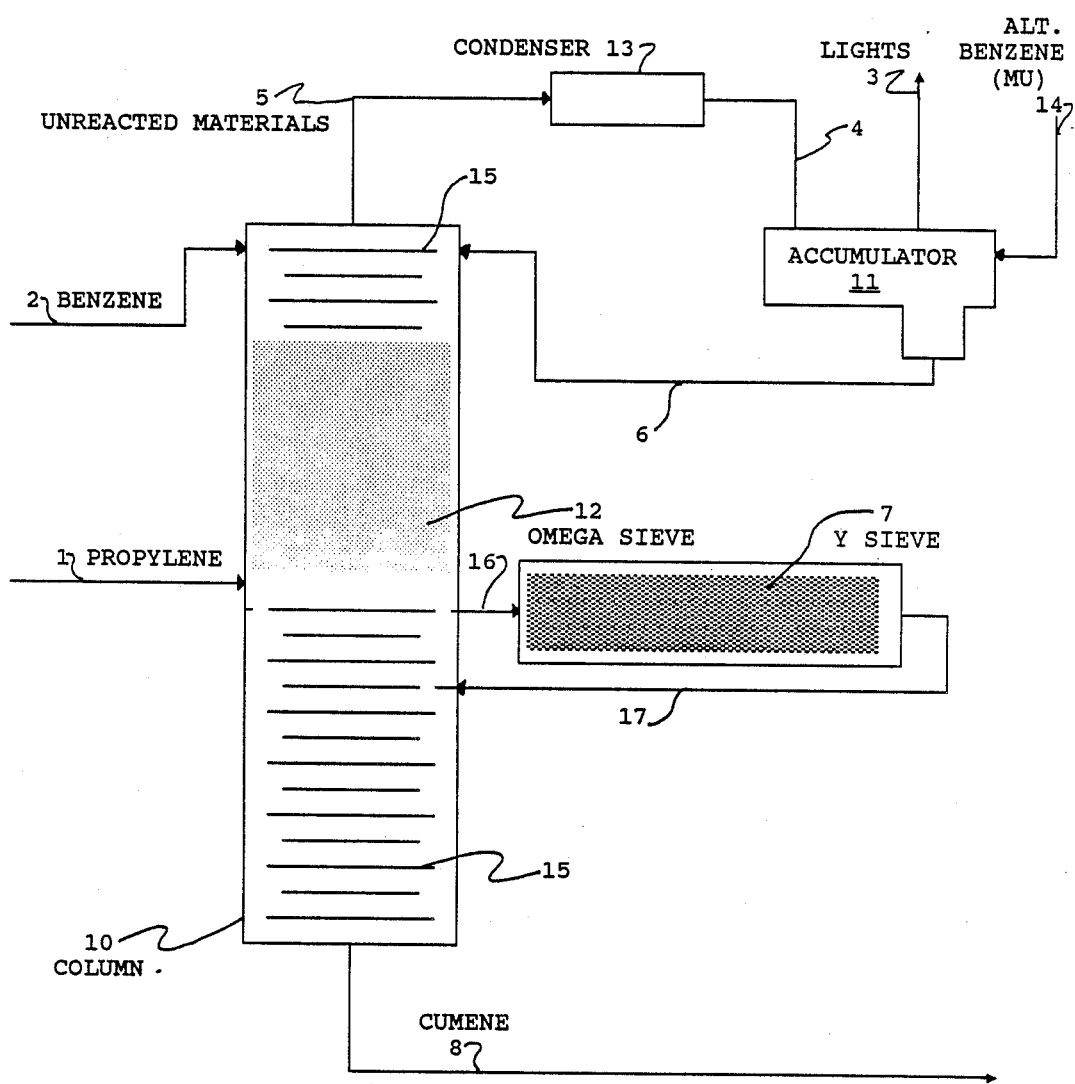
FIG. 2 is a schematic representation of an alternative embodiment of one species of the present invention for producing cumene wherein the type Y catalyst is not in the reactor distillation column.

FIG. 2 shows the embodiment wherein the Omega catalyst is in the distillation reactor as described before, except that the type Y sieve is outside of the column. A portion (any amount up to 100%) of the mid-reflux of the column is removed via line 16 an passed through the type Y sieve then back via 17 to the lower portion of the column containing conventional distillation trays 15.

Such conventional items as valves, reboilers, slip streams, etc. are not shown, but would be obvious expedients to those setting up such equipment.

The mole ratio of benzene to propylene in the column may be in the range of 2 to 100:1, preferably 2 to 50:1 and more desirably about 2 to 10:1. The greater the excess of benzene the more the selectivity to the monosubstituted product is improved. Alkylation is forced to completion, since the simultaneous and concurrent fractionation and removal of the alkylation product from the distillation column reactor does not allow the products to contribute to the reverse reaction (Le Chatelier's Principle). However, very large molar excesses of benzene require a very high reflux ratio, and a low unit productivity. In this reaction the propylene is the most volatile component and it is desirable to react it rather than have some carried off overhead. The presence of propylene or other lower boiling olefin in the tower with benzene will result in a small but detectable temperature depression in the tower where such lower boiling olefins are present as entities and unreacted. As the propylene is reacted with benzene, the depressing effect is diminished and furthermore, the reaction, which is exothermic, also diminishes the effect. The magnitude of the temperature depression immediately above the propylene feed is a measure of the concentration of propylene in the system, that is, the larger the concentration of the propylene, the greater the depression of the temperature where the benzene and propylene are initially together and yet unreacted. For this particular system the concentration of propylene to provide a given temperature depression can be determined and plotted. Thus, by maintaining a specific temperature at the point of maximum temperature depression by adjusting the propylene feed, a given ratio of propylene to benzene can be maintained in a simple and expedient manner. More significantly, the maintenance of the depression at a given temperature can assure that substantially all of the propylene will be reacted prior to the end of the catalyst bed and overhead exit, if the corresponding propylene concentration has been determined to produce that effect.

The present alkylation reaction can be carried out at sub-through super atmospheric pressure, e.g., 0.20 to 40 atmospheres. The temperature will vary depending on the reactants and product. Furthermore, the temperature along the column will be as in any distillation column, the highest temperature will be in the bottom and the temperature along the column will be the boiling point of the composition at that point in the column under the particular conditions of pressure. Moreover, the exothermic heat of reaction does not change the temperature in the column, but merely causes more boil up. However, the temperatures within the column with the above considerations in mind will generally be in the range of 50° C., e.g. 70° C. to 500° C. and more preferably in the range of about 80° C. to 300° C. at pressures of 0.5 to 20 atmospheres.

In a preferred embodiment the alkylation reaction is carried out by increasing the liquid level in the reaction distillation zone containing the Omega type molecular sieve. This is achieved by a liquid flow restrictor between the reaction distillation zone and the lower distillation zone. That is, the vapor from below may rise up to (and through) the reaction distillation zone as in a conventional or prior operation but a portion of the liquid is maintained there. If a single distillation column reactor is used, a conventional distillation tray with the downcomer area blocked is located between the reaction distillation zone and the distillation zone. A by pass line for liquid flow is provided about the tray and a valve is provided in the liquid flow conduit to restrict liquid downflow and thereby to build up a liquid level above that tray just below the catalyst bed. Alternatively a perforated plate may be used to support the catalyst and cause a liquid pressure drop in the column thus building up a level in the catalyst. If the two column system is used, then a valve or other restriction means is placed in the liquid flow line between the two columns.

While the particular position of the liquid level has been described above to be at the lower end of the reaction distillation zone, it could just as easily be placed anywhere in the catalyst bed depending upon the desired reactions.

The term "liquid level" is used herein to mean an increased density of the material in the reaction distillation zone over that of a pure distillation as distinguished to a continuous liquid phase. The phase system as present in the reaction distillation zone is physically a froth. This is the result of the vapor traveling up through the liquid retained in the zone.

Another way of viewing this is that in normal distillation there is a vapor with liquid (internal reflux) trickling down through the vapor and contacting the catalyst whereas in the present "flooded" system the vapor is traveling up through a liquid phase to create the froth or foam.

Hence in essence the benefits of the distillation are still obtained, i.e., separating the various components by the distillation whereas the increased liquid volume in contact with the catalyst improves the synthesis reaction. This method of operation is more fully described in commonly owned U.S. patent application Ser. No. 07/328,487, which is incorporated herein by reference.

EXAMPLE 1

The reactor was a 3 inch diameter pilot distillation tower having a 29 foot section packed with molecular sieve catalyst contained in glass cloth pockets twisted with demister wire as described above.

Two runs were carried out under substantially the same conditions using a Y type and Omega molecular sieve respectively. The results of the two runs are set out in Table I. Although the Omega catalyst showed better selectivity for cumene, the high content of olefin (indicated by the high bromine number) made the product commercially unacceptable.

TABLE I

| Run | 1 | 2 |
| --- | --- | --- |
| Catalyst | Y-82* | Omega |
| Mid-reflux Analysis, Wt. % | | |
| Benzene | 78.09 | 78.00 |
| Cumene | 17.01 | 18.12 |
| DIPB | 3.78 | 2.86 |
| TIPB | 0.29 | 0.15 |
| Wt. ratio, | | |
| Cumene/DIPB + TIPB | 4.2 | 6.0 |
| Selectivity | | |
| Benzene to cumene | 85.1 | 89.1 |
| Bromine No. of cumene product | 6 | >40 |

*Product of Union Carbide Corporation

EXAMPLE 2

Samples of the mid internal reflux from runs using the Omega sieve were collected and combined and fed over a Y-82 mole sieve catalyst (Linde) at 310° F. (LHSV 3 to 11) in a ⅜ inch isothermal reactor (as represented by FIG. 2). Analysis by chromatography and bromine number indicated that the olefins were removed to an acceptable level by the use of the Y-82 catalyst. Bromine titration is an accepted indication of the amount of olefins in a liquid. The propylene remaining in the mid-reflux sample was reacted to produce more cumene, and high cumene/dipropylbenzene ratio was improved due to some transalkylation obtained with the Y-82 as shown in Table II below.

TABLE II

| | Feed | Product 3 LHSV | Product 11 LHSV |
| --- | --- | --- | --- |
| Cumene, wt. %[1] | 90 | 95 | 92.6 |
| Cumene/dipb wt ratio | 9 | 20 | 12.6 |

[1] $\frac{\text{Cumene} \times 100}{\text{Cumene} + \text{DIPB} + \text{TIPB} + \text{HE}}$ (excludes benzene)

Complete analysis of the feed and product are given in Table III below. The bromine number of the product was 4 which compares with the bromine number of 102 obtained on tower bottoms when using the Omega sieve alone.

TABLE III

REACTION OF OMEGA CATALYZED MID-REFLUX OVER Y 82 CATALYST

| Compound | Feed, wt. % | Product 3 LHSV | Product 11 LHSV |
| --- | --- | --- | --- |
| $C_3=$ | 0.258 | 0.000 | 0.000 |
| Unknown | 0.006 | 0.000 | 0.014 |
| Benzene | 84.488 | 82.784 | 83.013 |
| Unknown | 0.158 | 0.132 | 0.155 |
| Toluene | 0.018 | 0.030 | 0.017 |
| Unknown | 0.124 | 0.024 | 0.012 |
| Unknown | 0.032 | 0.031 | 0.024 |
| Unknown | 0.003 | 0.024 | 0.000 |
| Cumene | 13.386 | 16.152 | 15.437 |
| DIPB | 0.460 | 0.543 | 0.763 |
| DIPB | 0.192 | 0.000 | 0.016 |
| DIPB | 0.766 | 0.280 | 0.433 |
| TIPB | 0.052 | 0.000 | 0.016 |
| Bromine No. | >100 | 4 | 12.6 |

The invention claimed is:
1. A process for the production of cumene by the alkylation of benzene with propylene comprising the steps of:
  (a) feeding a stream containing propylene into a distillation reactor column at a point below a bed of Omega molecular sieve catalyst prepared as distillation structures;
  (b) feeding benzene into said distillation reactor column at a point above said bed of Omega molecular sieve catalyst;
  (c) concurrently in said distillation reactor column:
    (1) reacting a portion of said propylene with said benzene within said bed of Omega molecular sieve catalyst to form a reaction mixture containing cumene, unreacted benzene, unreacted propylene and other reaction products, said other reaction products including dipropylbenzene and dimerized propylene, and
    (2) fractionally distilling said reaction mixture within said bed of Omega molecular sieve catalyst to partially separate said cumene from said unreacted benzene, said unreacted propylene and said other reaction products forming a liquid phase containing cumene, unreacted benzene, unreacted propylene and other reaction products, and a gaseous phase substantially free of said cumene;
  (d) contacting said liquid phase with a bed of zeolite Y molecular sieve catalyst to preferentially react said unreacted benzene contained therein with said unreacted propylene and propylene dimer and said dipropylbenzene contained therein to form additional cumene;

(e) after contact with said zeolite Y molecular sieve catalysts, fractionally distilling said liquid phase in said distillation reactor column into said bed of Omega molecular sieve catalyst;

(f) withdrawing cumene from a point below said bed of Omega molecular sieve catalyst; and (g) withdrawing unreacted benzene and unreacted propylene at a point above said bed of Omega molecular sieve catalyst.

2. The process according to claim 1 wherein said zeolite Y molecular sieve catalyst is positioned in said distillation reactor column below said Omega molecular sieve catalyst and adapted to serve a distillation structure.

3. The process according to claim 1 wherein said zeolite Y molecular sieve catalyst is positioned outside of said distillation reactor column.

4. A process for the alkylation of benzene with propylene to produce cumene in a distillation reactor column having an upper bed of Omega molecular sieve catalyst and a lower bed of Y zeolite molecular sieve catalyst, comprising the steps of:

(a) feeding a stream containing propylene into said distillation reactor column at a point below said bed of Omega molecular sieve catalyst;

(b) concurrently feeding benzene into said distillation reactor column at a point above said bed of Omega molecular sieve catalyst;

(c) concurrently in said distillation reactor column:
  (1) reacting a portion of said propylene with said benzene within said bed of Omega molecular sieve catalyst to form a reaction mixture containing cumene, unreacted benzene, unreacted propylene and other reaction products, said other reaction products including dipropylbenzene and dimerized propylene,
  (2) fractionally distilling said reaction mixture within said bed of Omega molecular sieve catalyst to partially separate said cumene from said unreacted benzene, said unreacted propylene and said other reaction products forming a liquid phase containing cumene, unreacted benzene, unreacted propylene and other reaction products, and a gaseous phase substantially free of said cumene,
  (3) contacting said liquid phase with said lower bed of zeolite Y molecular sieve catalyst to preferentially react said unreacted benzene contained therein with said unreacted propylene and propylene dimer and said dipropylbenzene contained therein to form additional cumene, and
  (4) fractionally distilling said liquid phase in said lower bed of zeolite Y molecular sieve catalyst to separate any unreacted benzene contained therein as a vapor back up said distillation reactor column into said upper bed of Omega molecular sieve catalyst;

(d) withdrawing cumene from a point below said lower bed of zeolite Y molecular sieve catalyst; and (e) withdrawing unreacted benzene and unreacted propylene at a point above said upper bed of Omega type molecular sieve catalyst.

5. The process of claim 4 wherein there is a molar excess of said benzene to said propylene in said distillation column reactor.

6. The process of claim 5 wherein substantially all of said propylene is reacted with said benzene.

7. The process of claim 4 wherein a portion said unreacted benzene is condensed and returned to said distillation column reactor at a point above said upper bed of Omega molecular sieve catalyst as reflux.

8. The process of claim 7 wherein make up benzene is added to said distillation column reactor in a molar ratio of benzene to propylene of 1:1 and a molar excess of benzene to propylene is maintained by said reflux.

9. The process of claim 8 wherein said make up benzene is added to said reflux.

10. The process of claim 4 wherein the temperature in said upper bed of Omega molecular sieve catalyst at the point of said propylene feed is the boiling point of said benzene at the operating pressure of said distillation column reactor.

11. The process of claim 5 wherein 2 to 100 moles of benzene per mole of propylene are present.

12. The process of claim 11 wherein from 2 to 50 moles of benzene per mole of propylene are present.

13. The process of claim 12 wherein from 2 to 10 moles of benzene per mole of propylene are present.

14. The process of claim 4 wherein the operating pressure in said distillation column reactor is in the range of 0.5 to 20 atmospheres.

15. The process of claim 14 wherein the temperature is in the range of 80° to 300° C.

16. The process according to claim 1 wherein the downward flow of internal reflux is restricted at selected points in said reaction distillation zone to maintain a liquid level above the restriction for additional contact and reaction of the liquid and distillation vapors with the Omega molecular sieve catalyst.

17. The process according to claim 2 wherein the downward flow of internal reflux is restricted at selected points in said reaction distillation zone to maintain a liquid level above the restriction for additional contact and reaction of the liquid and distillation vapors with the Omega molecular sieve catalyst.

18. The process according to claim 3 wherein the downward flow of internal reflux is restricted at selected points in said reaction distillation zone to maintain a liquid level above the restriction for additional contact and reaction of the liquid and distillation vapors with the Omega molecular sieve catalyst.

19. The process according to claim 4 wherein the downward flow of internal reflux is restricted at selected points in said reaction distillation zone to maintain a liquid level above the restriction for additional contact and reaction of the liquid and distillation vapors with the Omega molecular sieve catalyst.

20. The process according to claim 7 wherein the downward flow of internal reflux is restricted at selected points in said reaction distillation zone to maintain a liquid level above the restriction for additional contact and reaction of the liquid and distillation vapors with the Omega molecular sieve catalyst.

21. The process according to claim 8 wherein the downward flow of internal reflux is restricted at selected points in said reaction distillation zone to maintain a liquid level above the restriction for additional contact and reaction of the liquid and distillation vapors with the Omega molecular sieve catalyst.

22. The process according to claim 11 wherein the downward flow of internal reflux is restricted at selected points in said reaction distillation zone to maintain a liquid level above the restriction for additional contact and reaction of the liquid and distillation vapors with the Omega molecular sieve catalyst.

* * * * *